United States Patent
Brunk (10) Patent No.: US 7,252,382 B2
(45) Date of Patent: Aug. 7, 2007

(54) APPARATUS AND METHOD FOR MEASURING DIFFERENCES IN THE TRANSMISSION OF LIGHT THROUGH A LENS OF AN EYE

(76) Inventor: S. Fred Brunk, 2929 E. 69th St., Tulsa, OK (US) 74136-4541

( * ) Notice: Subject to any disclaimer, the term of this patent is extended or adjusted under 35 U.S.C. 154(b) by 572 days.

(21) Appl. No.: 10/791,848

(22) Filed: Mar. 4, 2004

(65) Prior Publication Data

US 2005/0195362 A1    Sep. 8, 2005

(51) Int. Cl.
    *A61B 3/02*    (2006.01)
(52) U.S. Cl. .................................... 351/239; 351/242
(58) Field of Classification Search ............... 351/239, 351/237, 246, 3, 222, 241–244; 600/530
    See application file for complete search history.

(56) References Cited

U.S. PATENT DOCUMENTS

| | | | |
|---|---|---|---|
| 2,462,485 A | 2/1949 | Freeman | |
| 3,801,188 A * | 4/1974 | Hunt et al. | 351/237 |
| 3,844,641 A * | 10/1974 | Nowak | 351/201 |
| 3,970,376 A * | 7/1976 | Ledl | 351/242 |
| 4,212,520 A | 7/1980 | Klimsa | |
| 4,327,973 A | 5/1982 | Raif | |
| 4,365,873 A | 12/1982 | Ginsburg | |
| 4,615,594 A | 10/1986 | Task | |
| 4,711,542 A | 12/1987 | Ichihashi et al. | |
| 4,848,898 A | 7/1989 | Massof | |
| 5,078,486 A * | 1/1992 | Evans | 351/243 |
| 5,430,510 A * | 7/1995 | Pynson | 351/239 |
| 5,609,159 A | 3/1997 | Kandel et al. | |
| 5,864,364 A * | 1/1999 | Ohyama et al. | 348/211.14 |
| 6,210,006 B1 | 4/2001 | Menozzi | |
| 6,220,708 B1 | 4/2001 | Koest | |
| 6,379,007 B1 | 4/2002 | Farb | |
| 6,851,809 B1 * | 2/2005 | Sachtler | 351/242 |
| 2004/0061835 A1 * | 4/2004 | Chen et al. | 351/242 |

FOREIGN PATENT DOCUMENTS

| | | |
|---|---|---|
| DE | 199 10 743 | 9/2000 |
| WO | WO 99/15071 | 4/1999 |

* cited by examiner

*Primary Examiner*—Huy Mai
(74) *Attorney, Agent, or Firm*—Richard C. Litman (57) ABSTRACT

The apparatus for measuring differences in the transmission of light through a lens of an eye is an eye chart has two main sections including a test section that displays a shade of a test color and a reference section that displays either a spectrum of shades, or a different shade of, the test color. The chart is displayed in a box, projected on a wall or displayed as a chart hung on a wall. The chart is illuminated using a constant or variable intensity light source. A patient is required to find or make a match between the shades disposed on the chart. When the variable intensity light is used, the patient will be required to adjust the light intensity of the section it illuminates until a match in color shades is made. The chart may be used in conjunction with a Snellen eye chart.

17 Claims, 6 Drawing Sheets

APPARATUS AND METHOD FOR MEASURING DIFFERENCES IN THE TRANSMISSION OF LIGHT THROUGH A LENS OF AN EYE

BACKGROUND OF THE INVENTION

1. Field of the Invention

The present invention relates to devices for measuring differences in the transmission of light through an eye. More particularly, the invention relates to a non-invasive device that uses shades of color and brightness of color to determine whether the eye is impaired, e.g., by cataracts.

2. Description of the Related Art

Eye examiners perform a number of tests to determine the health of an eye. Some tests gauge the eye's health and determine ailments based on the amount of light entering or, on the contrary, leaving the eye. A cataract is one eye disease that can be detected based on the amount of light entering the eye. A cataract is defined as a clouding of a lens of an eye. The clouding of the lens blocks light entry into the eye. The amount of light entering the eye and reaching the retina is proportionally related to color perception. Hence, decreased light entry into the eye results in the eye perceiving a color as being a dark shade, while increased light entry into the eye results in the patient perceiving the color as being a light shade. Other conditions that affect light entry into the eye are thin abnormalities in the cornea or problems with the retina.

Current tests used to measure light entry into the eye measure the amount of light scattered back out of the eye, or require the use of computers. Some of these tests are invasive or are based on subjective, visual observation by an examiner, while others require the patient to perform complicated tasks. Theses tests do not measure light entry into the eye based on the patient's own ability to perceive color. Therefore, an apparatus and method is needed for measuring light entry into the eye that is non-invasive and is based on a patient's individual ability to perceive color.

U.S. Pat. No. 4,327,973, issued to Raif on May 4, 1982, describes an ophthalmoscopic instrument for measuring eye defects, such as cataracts and flares. The instrument splits a light beam into a first part and a second part. The first part is reflected off the back of the eye to a viewing station. The second part passes through a light scatterer then to the viewing station to be matched with the light of the first part. The amount of light reflected on the viewing station is quantified to determine the health of an eye.

U.S. Pat. No. 4,711,542, issued to Ichihashi et al. on Dec. 8, 1987, describes a device that photoelectrically detects the amount of backscattering resulting from a laser beam directed into the back of the eye to determine ophthalmic disease, such as cataracts. U.S. Pat. No. 5,609,159, issued to Kandel et al. on Mar. 11, 1997, describes a method and apparatus for noninvasive determination of a disease state of an eye. The test determines a patient's color mixing behavior by requiring the patient to manipulate lights of different wavelengths until a match is made. The patient's test results are then compared to a standard determined appropriate for their age group.

Several devices have been developed that test color vision in the eye by requiring a patient to discern symbols, patterns or to change a variable to match a fixed item. U.S. Pat. No. 6,379,007, issued to Farb on Apr. 30, 2002, describes an eye chart with distinct symbols and methods for vision testing. The chart displays a distinct set of numbers, letters or pictures useful in diagnosing loss of color vision and testing for neurological disorders or diseases.

German Patent Number 19,910,743 published on Sep. 14, 2000, and U.S. Pat. No. 6,220,708, issued on Apr. 24, 2001 to Koest, both describe a method and device for producing multicolored patterns to test color vision. The device transmits a time-controlled light through color segments that can be alternatively rotated into the beam of the light path.

U.S. Pat. No. 4,848,898, issued to Massof on Jul. 18, 1989, describes an apparatus for testing color vision. The device uses a mixture of yellow, red and green lights to determine color vision deficiencies, such as anomalous trichromacy and dichromacy. The lights are displayed in different patterns and light intensities.

U.S. Pat. No. 6,210,006, issued to Menozzi on Apr. 3, 2001, describes a color vision deficiency test. The test displays two separate fields, each being a different color. The first field is a fixed color such as yellow; the second field is a variable color being either green or red. The test subject is asked to determine which field corresponds to the color they are instructed to select. The test is then repeated with a different variable color. Other colors may be adjusted for other types of color deficiencies.

U.S. Pat. No. 2,462,485, issued to Freeman on Feb. 22, 1949, describes a means for testing a person's sensitivity to discriminating colors. Test plates are used having a number of chromatic spots arranged in color groups. A test subject is required to determine the number of colors that differ from the majority of colors.

U.S. Pat. No. 3,970,376, issued to Ledl on Jul. 20, 1976, describes an instrument to test color vision. The instrument comprises a number of colored glass panels that are grouped in pairs and are illuminated by a light. The glass panels include a plurality of filters to transmit light at different degrees. A test subject determines and compares the color intensity of the panels. The results tell whether or not a person is colorblind.

International Patent Number WO 99/15071, published on Apr. 1, 1999, describes a method and apparatus for testing and qualifying visual information from the eye using a virtual reality system. U.S. Pat. No. 4,169,285, issued to Walker on Sep. 25, 1979, describes a method for quantifying a person's color perception.

Other devices have been developed that test the visual acuity of the eye by testing a patient's ability to discern symbols or contrast and spatial frequency. U.S. Pat. No. 4,212,520, issued to Klimsa on Jul. 15, 1980, describes a device for testing visual acuity. The device comprises an opaque chart having a plurality of cutout openings in the shape of numbers or letters, and a contrast means disposed behind the cutouts.

U.S. Pat. No. 4,365,873, issued to Ginsburg on Dec. 28, 1982, describes a visual sensitivity test for spatial frequency and contrast sensitivity. U.S. Pat. No. 4,615,594, issued to Task on Oct. 7, 1986, describes a vision test chart. The chart displays a number of test shapes organized over a background where both the shapes and the background each have its own pre-selected luminance level. The chart tests a subject's ability to perceive contrast, specifically, contrast in relation to size.

None of the above inventions and patents, taken either singly or in combination, is seen to describe the instant invention as claimed. Thus an apparatus and method for measuring differences in the transmission of light through a lens of an eye solving the aforementioned problems is desired.

SUMMARY OF THE INVENTION

The apparatus for measuring differences in the transmission of light through a lens of an eye is an eye chart having two main sections. One section is a test section that displays a shade of a color, and the other section is a reference section that displays either a spectrum or a different shade of the color shown in the test section. The chart is displayed in a box, projected on a wall or displayed as a wall hanging. The chart is illuminated using a constant intensity light or a variable intensity light, such as a dimmer. A patient is required to find or make a match between the shades disposed on the chart. When the variable intensity light is used, the patient will be required to adjust the light intensity of the section it illuminates until a match in color shades is made. The chart may be used in conjunction with a Snellen eye chart.

The method for measuring differences in the transmission of light would include displaying the chart to a patient, illuminating the chart, instructing the patient to match the color shade of the test section with one of the shades in the reference section, and recording an indicia associated with the shade selected by the patient, thereby quantifying the color perception.

By periodically testing the patient's perception of color, the examiner can quantitatively gauge the patient's normal perception of color. Subsequent changes in the patient's perception in color may have significance in indicating the onset of pathological disease processes, such as cataracts, and may be of value in formulating a course of treatment, viz., selection of substitute or corrective lenses.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
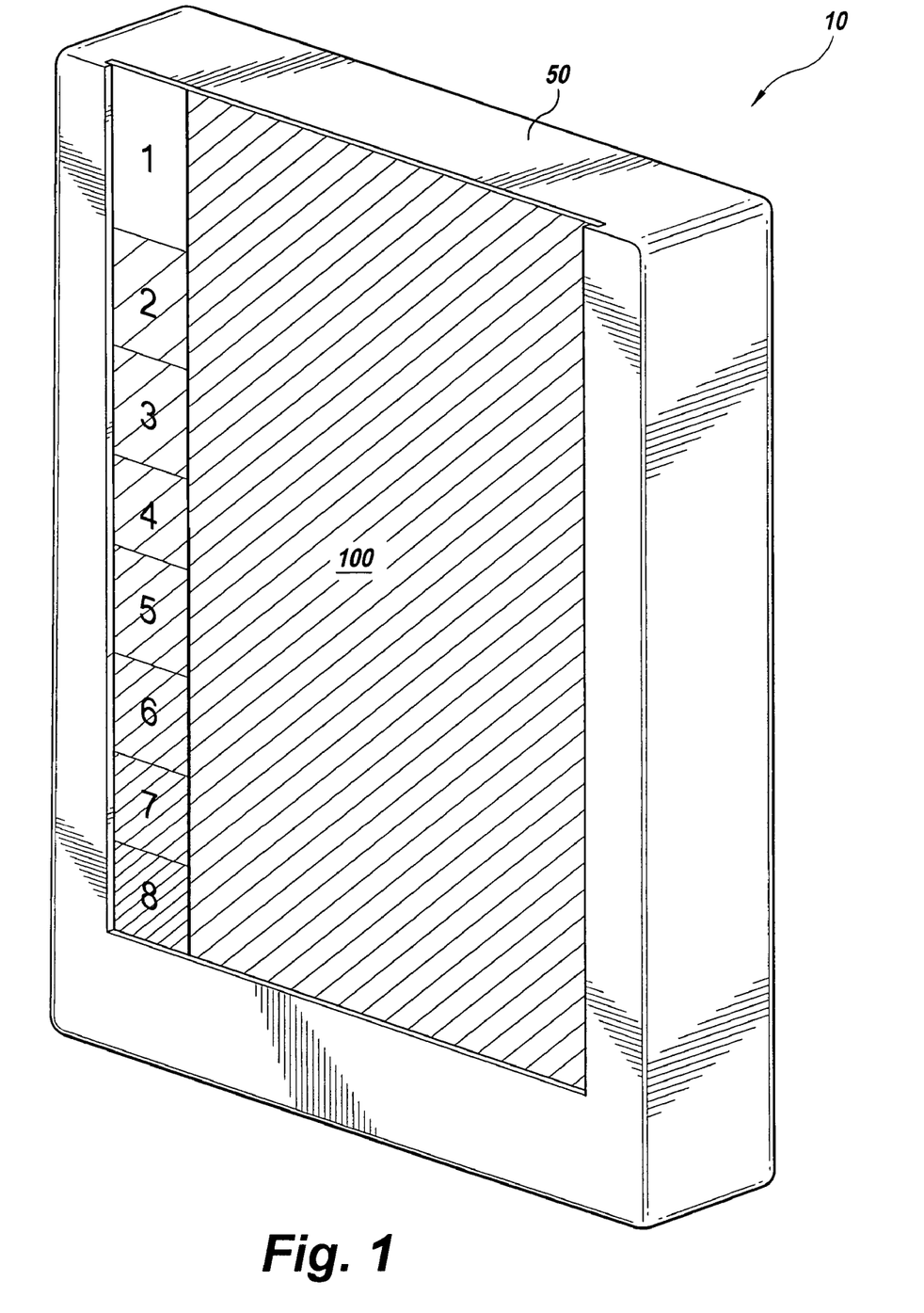
FIG. 1 is a perspective view of an apparatus for measuring differences in the transmission of light through a lens of an eye according to the present invention showing an eye chart and a display device.

The present invention describes an apparatus and method for measuring differences in the transmission of light through a lens of an eye. As shown in FIG. 1, the apparatus 10 comprises an eye chart 100 and a display device 50. The eye chart 100 shown in FIG. 1 only one embodiment of a chart that can be used with the display device 50. Other alternative embodiments will be discussed further below.

The type of display device 50, shown in FIG. 1, is an illuminator cabinet. The illuminator cabinet holds the chart 100 and projects light through the back of the chart 100. Other types of display devices 50 may be used to display the chart 100, such as an enclosed box 60 described below with reference to FIG. 6, or a projector. Alternatively, the chart 100 may not be displayed in the device 50, but rather may be displayed on a wall in the form of a paper chart that is hung upon a wall.

Figure 2:
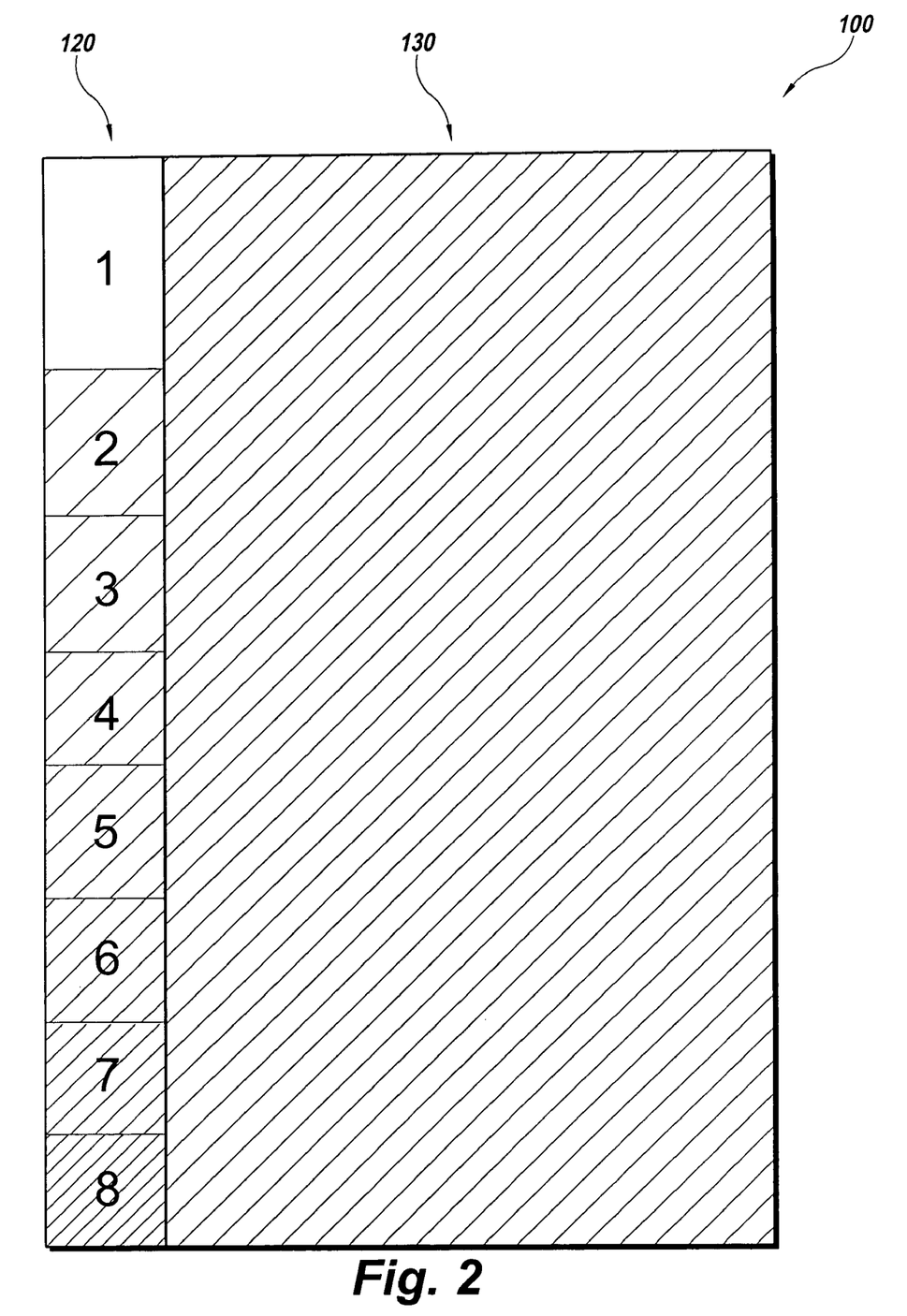
FIG. 2 is a front view of the eye chart of the apparatus of FIG. 1 according to the present invention.

Referring now to FIG. 2, the eye chart 100 is shown in detail, having a reference section 120 and a test section 130. Both sections 120, 130 display shades of one color. The test section 130 displays one shade of the color and the reference section 120 displays a color spectrum of different shades of the same color, e.g., from light blue to dark blue. The sections 120, 130 are separated into defined sections with the reference section 120 being further separated into a plurality of subsections. Each subsection of the reference section 120 contains a different shade of the spectrum, with at least one of the shades representing the color shade of the test section 130. Each subsection of the reference section is identified by a unique indicia, such as a number, letter, symbol or shape. The subsections shown in chart 100 display number indicia 1 thorough 8 to uniquely identify each shade of the spectrum. The shades in the spectrum are preferably arranged in order from lightest to darkest; however, the shades may be arranged in random order as long as each shade is clearly identified by the indicia.

The apparatus 10, in particular the chart 100, is used to measure the amount of light entering the eye and disclose whether there is a light impairment in the eye. The amount of light entering the eye affects vision, such as color perception. When light entry into the eye is decreased, colors will be perceived as being dark. Conversely, with increased light entry into the eye, colors will be perceived as being light.

In use, the chart 100 is displayed in a display device 50 or as a wall hanging and a patient is asked to determine which color shade in the spectrum of the reference section 120 matches the color shade displayed in the test section 130. The patient identifies the match by indicia. The apparatus 10 can be placed preferably about fifteen to twenty feet away from the patient. However, the distance is not a critical factor in conducting the test.

In order to evaluate the amount of light entering the eye, there must be a light source used to illuminate the chart 100. The light source may have a constant light intensity, or a constant intensity light source may be used in conjunction with a variable intensity light source to illuminate the chart 100 from any direction. The constant light intensity source may be a light bulb, such as a fluorescent bulb having a fixed wattage level. The variable intensity light source is preferably a light having a dimmer in order to display a range of light intensities. Each light intensity level displayed by the dimmer is identifiable by a wattage level. An alternative way to use the variable intensity light source is by using different light bulbs having different wattages and turning each one on in isolation from the other bulbs.

The chart 100 is used to test the patient's ability to perceive color changes and correlate that to the amount of light impairment or light entry into the eye. When using a constant light source to illuminate the chart 100 the patient is instructed to determine which shade in the spectrum most closely matches the shade in the test section 130 and to indicate the match by naming the indicia associated with the reference color shade. When using the variable light intensity source and the constant light intensity source simultaneously to illuminate the chart 100, the patient is also required to make a match between the sections 120, 130.

When using a constant intensity light source and a variable intensity light source to illuminate the chart 100, the variable intensity light source is used to illuminate the test section 130 and the constant intensity light source illuminates the reference section 120. The variable intensity light adds a variable to the test used to measure light entry into the eye based on light intensity. The chart 100 using the variable intensity light would be illuminated at a high light intensity corresponding to a lighter shade in the spectrum of the reference section 130, then by a low light intensity corresponding to a darker shade in the spectrum. In each case, the patient would be asked to determine a match in shade color from the spectrum and to identify the match by indicia. The match is then also recorded as to the amount of wattage or voltage used to conduct that step of the test.

An alternative way to use the variable intensity light source with the apparatus 10 is by having the patient vary the light illuminating the test section 130 until it matches a pre-selected color shade identified by the indicia. Here again the wattage or voltage of the amount of light needed to make the match is recorded. In either case, the patient's results are recorded and quantified over time to detect and monitor any changes to light entry into the eye.

The apparatus 10, in particular the chart 100, is used to test both eyes together, and then each eye individually. The chart 100 helps to determine what the normal amount of light entering the eye is for that individual patient, and it also determines if there is light impairment in either eye. The patient's ability to perceive color is evaluated over time and quantified to determine the extent and progression, if any, of light impairment in the eye.

Figure 3:
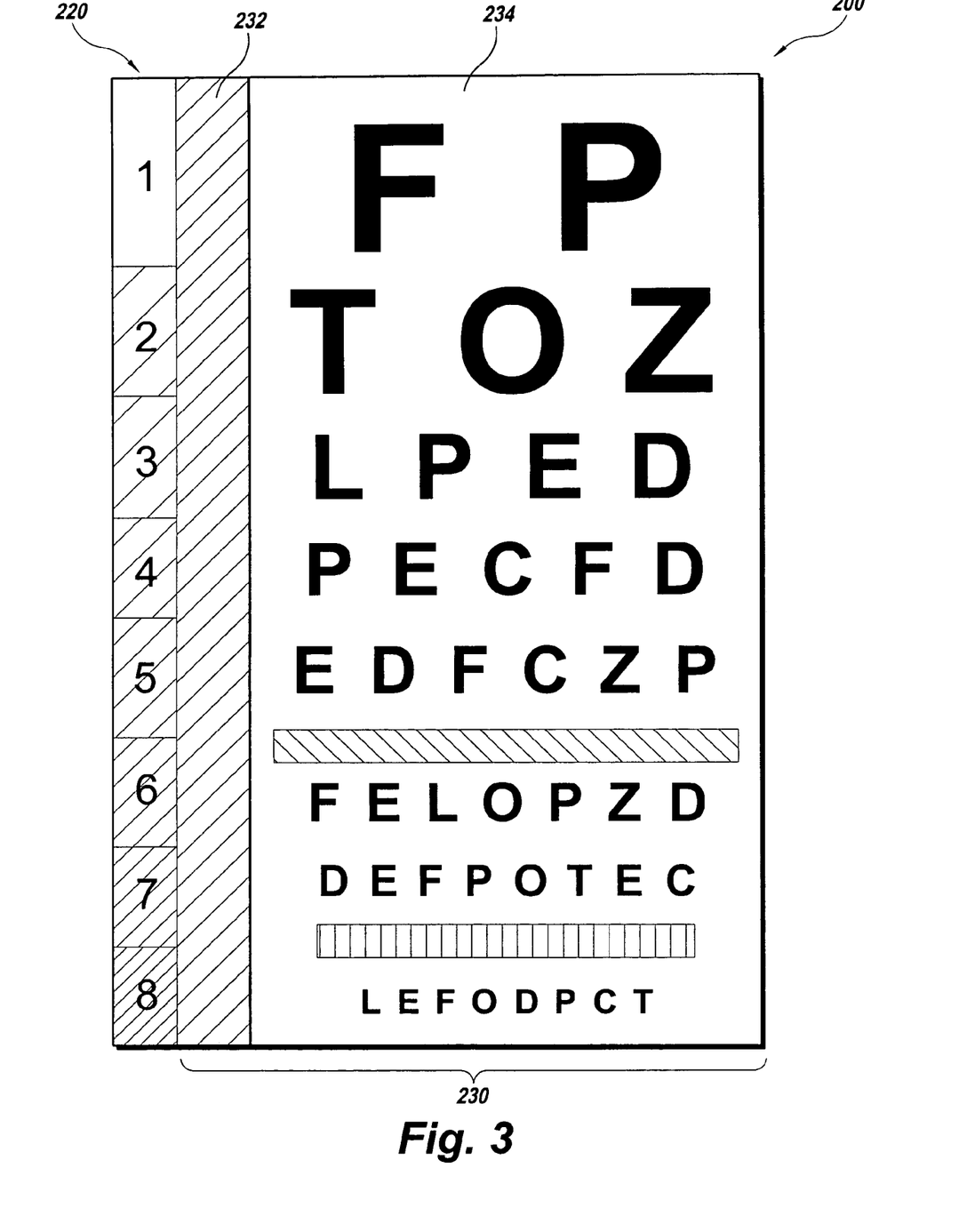
FIG. 3 is a front view of an alternative embodiment of the eye chart.

FIG. 3 shows an alternative eye chart embodiment 200. The chart 200 has a reference section 220 and a test section 230. Here, the test section 230 displays a shade of a color and the reference section 220 displays a spectrum of the same color as that shown in the test section 230. Both sections 220, 230 are further divided into subsections. The reference section 220 displays a plurality of subsections. Each subsection displays a different shade of the test color and an identifying indicia. The test section 230 is separated into two subsections, a color stripe 232 and a vision chart 234.

The color stripe 232 displays a test color shade that matches one of the reference color shades in the spectrum shown in the reference section 220. The vision chart 234 displays a Snellen Eye Chart; however, other types of vision charts may also be utilized with the eye chart 200, such as a Tumbling E chart, a Tumbling C chart, a hand chart, a symbol chart, or a reversed letter chart. The Snellen eye chart disposed in the vision chart section 234 displays letters in rows and also two color strips, a red strip and a green strip. The strips are standard features on the Snellen chart and are used to determine deuteranopia and protanopia.

Figure 4:
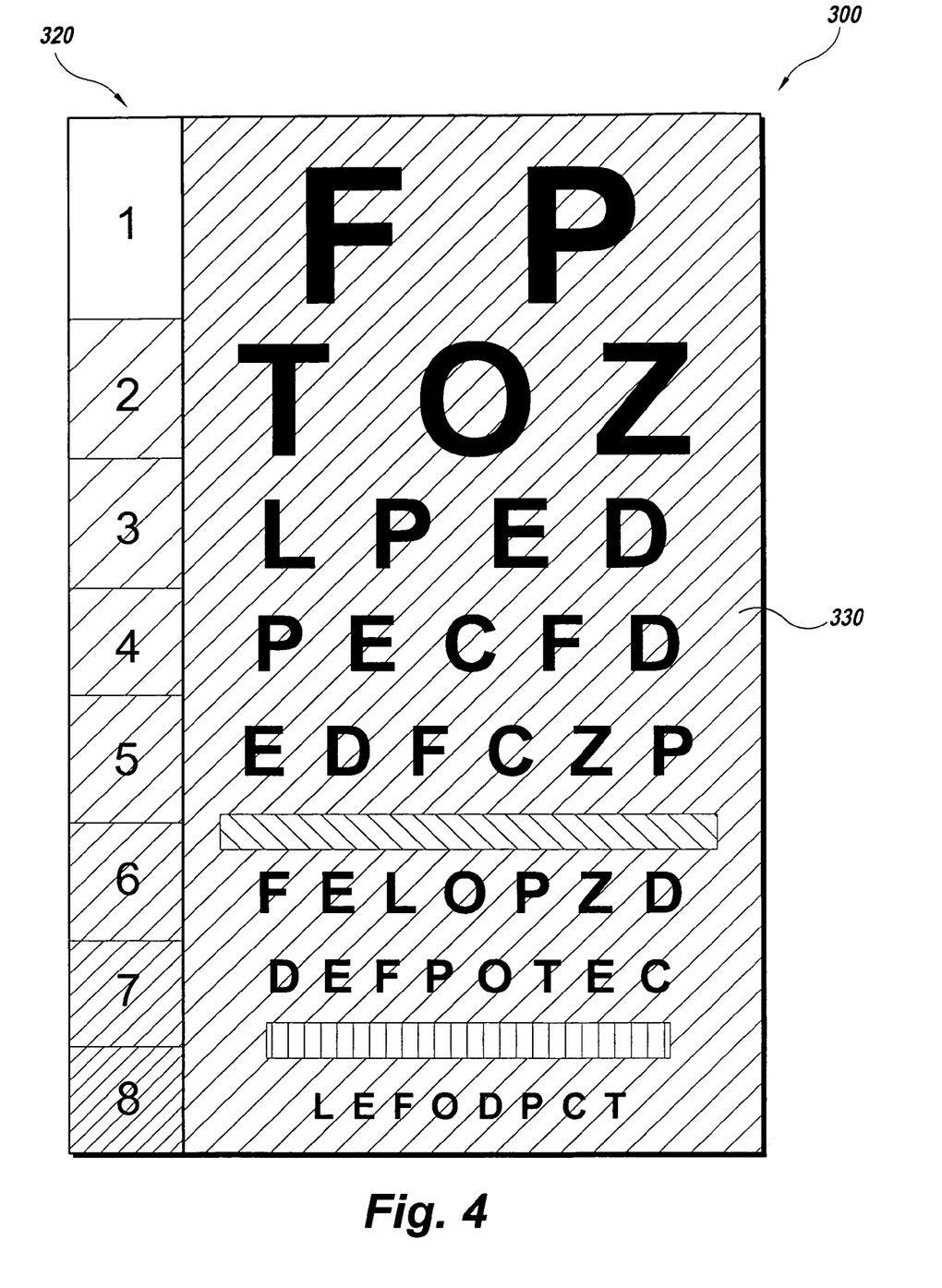
FIG. 4 is a front view of a third alternative embodiment of the eye chart.

FIG. 4 shows a third alternative eye chart embodiment 300. The chart 300 displays a reference section 320 and a test section 330. The test section 330 displays both a test color and the Snellen chart simultaneously. The reference section 320 displays a spectrum of the test color with each shade uniquely identified by an indicia and separated into subsections. Charts 200 and 300 would be used the same way as chart 100, being disposed in a display device 50 or as a chart hanging on a wall. Also the charts 200 and 300 could be illuminated using either a constant or variable intensity light source as described with respect to chart 100.

Figure 5:
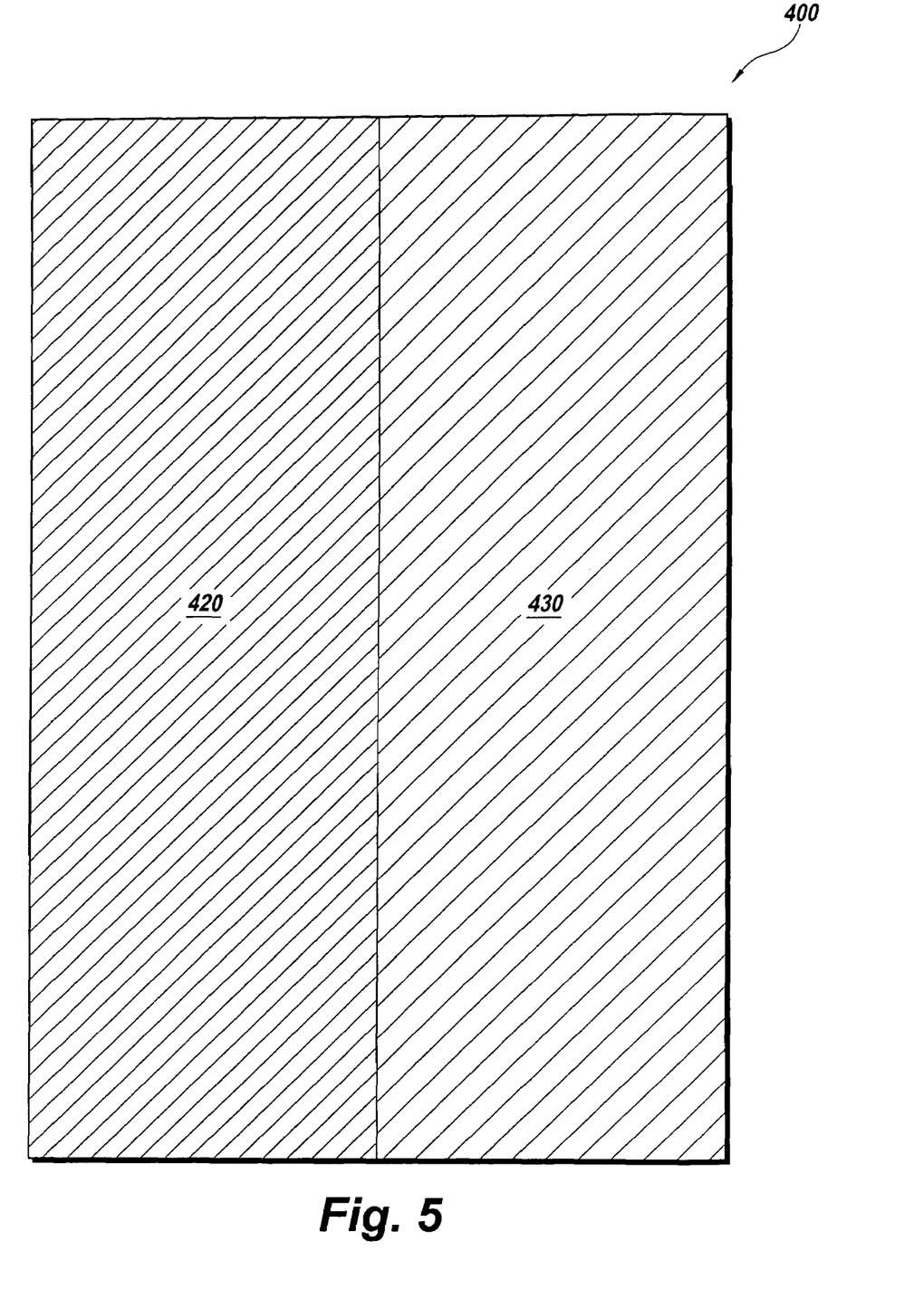
FIG. 5 is a front view of a fourth alternative embodiment of the eye chart.

FIG. 5 shows a fourth alternative eye chart embodiment 400. The eye chart 400 is divided into equal halves, where one of the halves is designated a reference section 420 and the other half is designated a test section 430. Chart 400, unlike charts 100, 200 and 300, only displays two shades of one color. Each shade is disposed in one of the two sections 420, 430. Chart 400 may be displayed in an illumination cabinet or similar display device 50, as shown in FIG. 1, in an enclosed box 60, as shown in FIG. 6, or using a projector.

Figure 6:
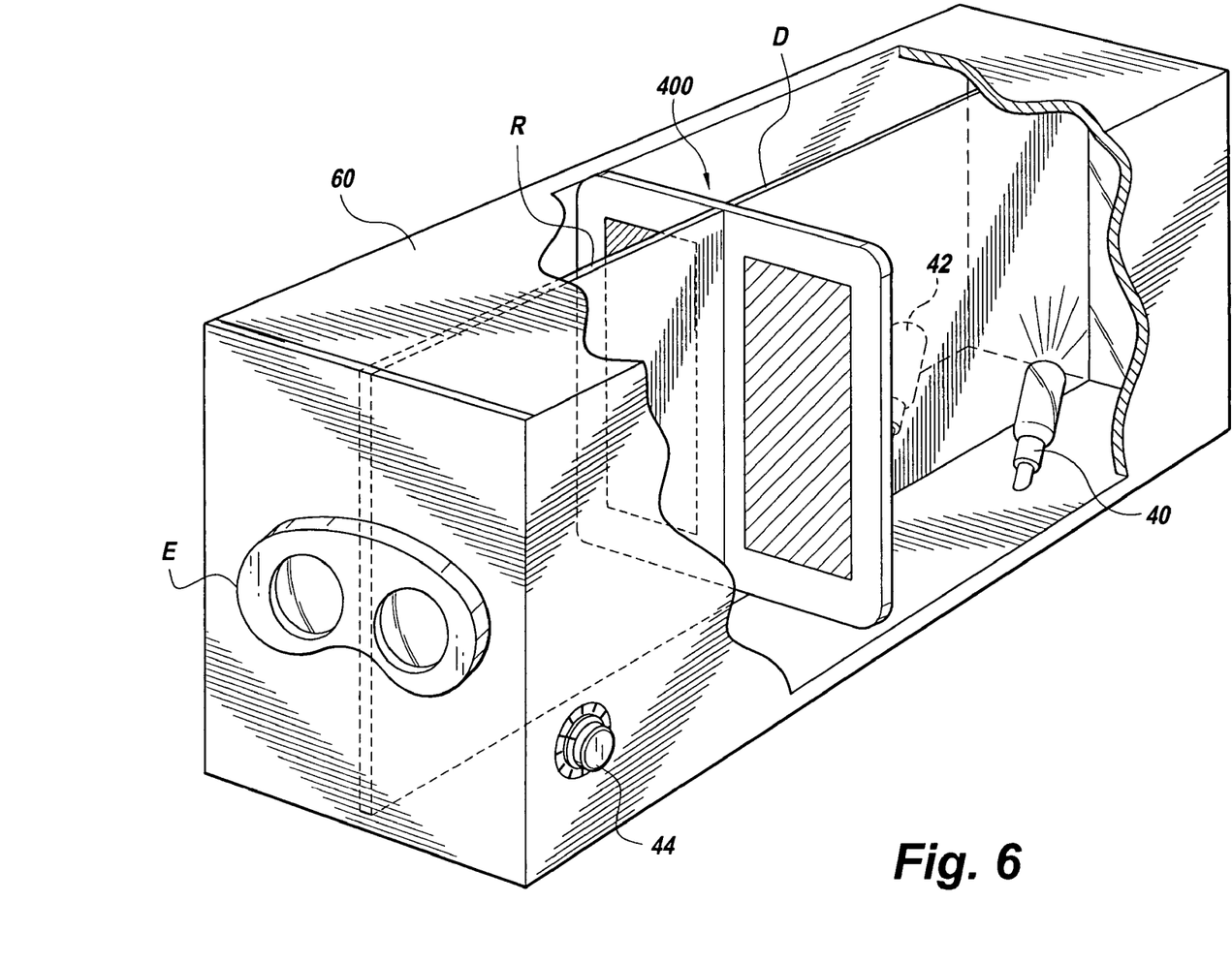
FIG. 6 is a perspective view of a display device for measuring differences in the transmission of light through a lens of an eye according to the present invention.

Chart 400 is best displayed in an enclosed box 60 having a controlled and separated light source, as shown in FIG. 6. The box 60 holds the chart 400 and has two light sources 40, 42 disposed behind each section 420, 430 of the chart 400. A divider D separates the light sources 40, 42 so that each light source 40, 42 only illuminates one section. The patient is directed to look through a dual eyepiece E disposed at one end of the box 60 to view the chart 400. A second divider R is disposed in the front of the box 60 between the chart 400 and the eyepiece E of the box 60 so each eye only sees one section 420, 430 of the chart 400. Here the patient is instructed to make the color shades between the sections 420, 430 match and appear as one uniform color by controlling the light source used to illuminate the sections. A light switch 44 or other controlling device connected to a dimmer is disposed on the box 60 for this purpose.

The sections 420, 430 of the chart 400 are illuminated using either a constant intensity light source to illuminate one section and a variable intensity light source to illuminate the other section, or two variable intensity light sources are used, one for each section. In use, the patient is placed before the chart 400 and asked to determine which section 420, 430 is darker. If one variable light source is used to illuminate one of the sections 420, 430, then the light intensity used to illuminate the section 420, 430 is varied until section 420, 430 matches the other section 430, 420 and the patient perceives both sections 420, 430 as one uniform shade of the color.

Alternatively, chart 400 could have its sections 420, 430 show the same shade of the color and the patient would be asked to determine which of the sections 420, 430 is perceived as darker, if at all, to determine which of the two eyes has a greater light impairment in the eye. When using two variable lights the variable light illuminating the section viewed by the impaired eye would be varied until both eyes perceive a color match between the two sections 420, 430. The amount of light entering the eyes is quantified by the amount of wattage or volts it took to illuminate the section 420, 430 until the patient could perceive one shade on the chart 400.

Each chart 100, 200, 300, 400 can be utilized individually or in combination to determine whether the patient has some sort of light impairment. Conditions that impair light entry into the eye include: cataracts, thin abnormalities in the cornea, Fuch's dystrophy or problems with the retina. By using charts 100, 200, 300, 400 the examiner would determine if there is a difference between the two eyes, quantitate the difference and follow the presence and progression of light impairment in an individual over time.

A fifth eye chart embodiment disposes the Snellen chart on a colored background. The fifth embodiment may be displayed using a projection, a wall cabinet or a simple wall hanging. This eye chart embodiment provides a screening device to test the perception of light between the two eyes. Here, the patient looks at the chart using each eye individually. If there is a difference in the light transmission through an eye then the eye perceiving the darker color is impaired. This initial test would be followed up using charts 100, 200, 300 and 400 to determine the extent and, over time, the progression of light impairment in the eye.

It is to be understood that the present invention is not limited to the embodiments described above, but encompasses any and all embodiments within the scope of the following claims.

I claim:

1. An apparatus for measuring differences in transmission of light through a lens of an eye of a patient using shades of color and brightness of color, comprising:
   a chart having a test section displaying a selected shade of a test color and a reference section simultaneously displaying a spectrum of shades of the test color including the selected shade;
   means for uniquely identifying each of the shades displayed in the spectrum of the reference section;
   means for illuminating the chart; and
   means for displaying the chart,
   whereby shades of color and brightness of color that are perceived by the eye are used to determine whether the eye has impaired transmission of light through the lens.

2. The apparatus for measuring differences according to claim 1, said means for uniquely identifying comprises a unique identifying indicia disposed on each of the shades of the spectrum.

3. The apparatus for measuring differences according to claim 1, further comprising a Snellen chart disposed on said chart.

4. The apparatus for measuring differences according to claim 1, wherein said means for illuminating comprises a constant intensity light source.

5. The apparatus for measuring differences according to claim 4, wherein said means for illuminating further comprises a variable intensity light source.

6. The apparatus for measuring differences according to claim 5, wherein said variable intensity light source includes a dimmer.

7. The apparatus for measuring differences according to claim 1, wherein said means for displaying said chart comprises an illumination cabinet.

8. The apparatus for measuring differences according to claim 1, wherein said means for displaying said chart comprises an enclosed box.

9. An apparatus for measuring differences in transmission of light through a lens of an eye using shades of color and brightness of color, comprising:
   a chart having a test section displaying solely a first shade of a test color and a reference section located adjacent to said test section and simultaneously displaying solely a second shade of the test color different from the first shade;
   a first light source for illuminating the test section;
   a second light source for illuminating the reference section, the second light source including means for varying illumination intensity produced by the light source; and
   means for displaying the chart,
   whereby shades of color and brightness of color that are perceived by the eye are used to determine whether the eye has impaired transmission of light through the lens.

10. The apparatus for measuring differences according to claim 9, wherein said first light source comprises a constant intensity light source.

11. The apparatus for measuring differences according to claim 10, wherein said second light source comprises a variable intensity light source.

12. The apparatus for measuring differences according to claim 11, wherein said variable light source includes a dimmer.

13. The apparatus for measuring differences according to claim 11, wherein said second light source comprises a plurality of constant intensity light sources of different intensities and at least one light switch electrically connected to said plurality of light sources for electrically switching one of the light switches on at a time.

14. The apparatus for measuring differences according to claim 9, wherein said means for displaying comprises a display box.

15. The apparatus for measuring differences according to claim 9, wherein said first light source comprises a variable intensity light source in order to adjust the test color to any desired shade.

16. A method for measuring differences in transmission of light through a lens of an eye of a patient using shades of color and brightness of color, comprising the steps of:
   displaying a chart having a test section and a reference section, the test section displaying a shade of a test color and the reference section simultaneously displaying only a spectrum of shades of the test color identified by a unique indicia;
   illuminating the test section and the reference section with at least one light source;
   instructing the patient to match the shade of the test color shown in the test section to one of the shades of the spectrum of the reference section; and
   recording the shade from the reference section selected by the patient identifying the unique indicia,
   whereby shades of color and brightness of color that are perceived by the eye are used to determine whether the eye has impaired transmission of light through the lens.

17. The method for measuring differences according to claim 16, wherein said at least one light source comprises a variable intensity light source, the method further comprising the step of adjusting the intensity of light illuminating the test section to a desired shade of the spectrum.

* * * * *